(12) United States Patent
Um et al.

(10) Patent No.: US 10,010,561 B2
(45) Date of Patent: *Jul. 3, 2018

(54) METHOD OF TREATING CANCER USING HIGH EFFICIENCY SELF-ILLUMINATIVE NANOCOMPLEXES AND METHOD OF MANUFACTURING THE SAME

(71) Applicant: Research & Business Foundation Sungkyunkwan University, Suwon-si (KR)

(72) Inventors: Soong Ho Um, Seoul (KR); Woo Chul Song, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 176 days.

This patent is subject to a terminal disclaimer.

(21) Appl. No.: 14/688,439

(22) Filed: Apr. 16, 2015

(65) Prior Publication Data

US 2015/0297682 A1 Oct. 22, 2015

(30) Foreign Application Priority Data

Apr. 18, 2014 (KR) ........................ 10-2014-0046482

(51) Int. Cl.
| | | |
|---|---|---|
| *A61K 39/395* | (2006.01) | |
| *A61K 31/704* | (2006.01) | |
| *A61K 49/00* | (2006.01) | |
| *A61K 9/51* | (2006.01) | |
| *A61K 33/24* | (2006.01) | |
| *A61K 47/69* | (2017.01) | |

(52) U.S. Cl.
CPC .......... *A61K 31/704* (2013.01); *A61K 9/5115* (2013.01); *A61K 33/24* (2013.01); *A61K 47/6923* (2017.08); *A61K 49/0067* (2013.01); *C12Y 113/12007* (2013.01)

(58) Field of Classification Search
None
See application file for complete search history.

(56) References Cited

U.S. PATENT DOCUMENTS

| | | | | |
|---|---|---|---|---|
| 8,263,417 B2* | 9/2012 | Rao | ........................ | B82Y 15/00 435/7.1 |
| 9,163,048 B2* | 10/2015 | Um | .................... | A61K 47/4813 |
| 2012/0141382 A1* | 6/2012 | Shi | .......................... | B82Y 5/00 424/9.323 |
| 2012/0141550 A1* | 6/2012 | Maye | ................. | A61K 31/7042 424/400 |
| 2012/0269734 A1 | 10/2012 | Rao et al. | | |

FOREIGN PATENT DOCUMENTS

KR 10-2013-0041591 A 4/2013

OTHER PUBLICATIONS

So, Min-Kyung, et al. "Self-illuminating quantum dot conjugates for in vivo imaging." Nature Biotechnology 24.3 (2006): 339-343. Stanford, California, USA.

* cited by examiner

*Primary Examiner* — Laura B Goddard
*Assistant Examiner* — Meera Natarajan
(74) *Attorney, Agent, or Firm* — NSIP Law (57) ABSTRACT

The present disclosure relates to a method of treating cancer using a composition including a target-specific self-illuminative nanocomplex which includes a self-illuminative nanocomplex including a quantum dot and a modified self-illuminative protein (m-Rluc8), a targeted cancer-specific molecule and a hydrophilic polymer, and a method of preparing the composition. Since the high efficiency self-illuminative nanocomplex may have high target specificity by chemically binding to a target-specific molecule, it can be effectively used in cancer treatment using a nanometer-scale laser light source, and therefore it is expected to propose a new paradigm of nanoptic therapeutics.

14 Claims, 9 Drawing Sheets

Fig. 1

MASKVYDPEQRKRMITGPQWWARCKQMNVLDSFINYYDSEKHAENAVIFLHGNATSSYLWRHVVPHI
EPVARCIIPDLIGMGKSGKSGNGSYRLLDHYKYLTAWFELLNLPKIIFVGHDWGAALAFHYAYEHQDRIK
AIVHMESVVDVIESWDEWPDIEEDIALIKSEEGEKMVLENNFFVETVLPSKIMRKLEPEEFAAYLEPFKEGE
VRRPTLSWPREIPLVKGGKPDVVQIVRNYNAYLRASDDLPKLFIESDPGFFSNAIVEGAKKFPNTEFVKVKG
LHFLQEDAPDEMGKYIKSFVERVLKNEQ

METHOD OF TREATING CANCER USING HIGH EFFICIENCY SELF-ILLUMINATIVE NANOCOMPLEXES AND METHOD OF MANUFACTURING THE SAME

STATEMENT REGARDING GOVERNMENT RIGHTS

This invention was supported by a grant of the Korea Health Technology R&D Project through the Korea Health Industry Development Institute (KHIDI), funded by the Ministry of Health & Welfare, Republic of Korea (grant no. HI14C3301) and by Basic Science Research Programs through the National Research Foundation (NRF) funded by the Ministry of Science ICT and Future Planning (grant nos. 2013R1A1A1058670 and 2013R1A1A2016781). The government has certain rights in the invention.

CROSS-REFERENCE TO RELATED APPLICATION

This application claims priority to and the benefit under 35 U.S.C. § 119(a) of Korean Patent Application No. 10-2014-0046482, filed on Apr. 18, 2014 in the Korean Intellectual Property Office, the disclosure of which is incorporated herein by reference in its entirety for all purposes.

SEQUENCE LISTING

The instant application contains a Sequence Listing which has been submitted electronically and is hereby incorporated by reference in its entirety.

The present invention was undertaken with the support of Self-illuminative light-driven thermal cascade reaction-induced nanocomplexed medication and its prostate cancer therapeutic application No. 2016R1D1A1B03931270 grant funded by the Ministry of Science, ICT and Future Planning.

BACKGROUND

1. Field

The present disclosure relates to a method of treating cancer using a composition including a target-specific self-illuminative nanocomplex including a self-illuminative nanocomplex including a quantum dot and a modified self-illuminative protein (m-RlucS), a targeted cancer-specific molecule and a hydrophilic polymer.

2. Description of Related Art

A laser light source used in conventional medical fields is too much dependent on the skill of an experimenter, and has a considerably low in vivo transmittance. In other words, today, since a laser therapy used for skin tissues needs a relatively large laser irradiated area in spite of an excellent resolution of the laser light source, a side effect of damage to normal cells around a target tissue that is necessarily treated should be considered. In addition, since the in vivo transmittance of the laser is very insignificant, there is a substantial limitation to apply a laser therapy to internal organs in addition to epithelial tissues and mucosal tissues in contact with an air.

To make up for such disadvantages and utilize superiority of the laser light source (high resolution and highly-integrated energy transferring performance), today, a method of controlling a laser irradiated region using a computer, or disposing a laser light source unit directly on a target organ using a da Vinci robot after local incision of an epithelial tissue to directly irradiate an internal organ with a laser is used. However, it is hard to say that the above-described problems are fundamentally overcome since these methods can be only used in a state in which a target region is fixed such as a cornea or external injuries remain after operation. Accordingly, to solve such problems, it is required to improve a more fundamental treating method, different from currently used methods.

SUMMARY

To overcome problems of the conventional art, the inventors developed a self-illuminative nanocomplex consisting of a nucleic acid having high target specificity, a modified self-illuminative protein having strong luminescence activity, polyethyleneglycol inhibiting a non-specific interaction, and a quantum dot having high fluorescence efficiency, and therefore completed the present disclosure.

However, technical objects to be accomplished by the present disclosure are not limited to the above-described objects, and other objects that are not described herein would be clearly understood from the following descriptions by those of ordinary skill in the art.

In one general aspect, the present disclosure provides a method of treating cancer, which includes treating a composition including the following components:

(a) a self-illuminative nanocomplex including a quantum dot and a modified self-illuminative protein consisting of an amino acid sequence of SEQ. ID. NO: 1; and (b) a gold nanoparticle complex binding to a linear nucleic acid containing an anticancer drug.

The anticancer drug may be selected from the group consisting of doxorubicin, daunorubicin, mitoxantrone and epirubicin.

The linear nucleic acid may have a thiol group at 5' end.

The linear nucleic acid may consist of a base sequence of SEQ. ID. NO: 3.

From the gold nanoparticles, cetyltrimethylammonium bromide (CTAB) may be removed.

The self-illuminative nanocomplex may emit light at 800 nm in the near-infrared region.

The cancer may be one selected from the group consisting of prostatic cancer, lung cancer, breast cancer, gastric cancer, liver cancer, rectal cancer, cystic duct carcinoma, colon cancer, pancreatic cancer, ovarian cancer, bronchial cancer and bladder cancer, or solid cancer overexpressing an antigen specific to another cancer.

In another general aspect, the present disclosure provides a method of preparing a composition for treating cancer, which includes the following operations:

(a) preparing an self-illuminative nanocomplex by mixing a quantum dot and a modified self-illuminative protein presented by an amino acid sequence of SEQ. ID. NO: 1 with a crosslinking agent;

(b) preparing a linear nucleic acid containing an anticancer drug by mixing a linear nucleic acid having a thiol group at 5' end with an anticancer drug in a molar ratio of 1:10 to 1:20;

(c) preparing a gold nanoparticle complex by mixing the linear nucleic acid containing the anticancer drug with gold nanoparticles from which CTAB is removed; and (d) mixing the self-illuminative nanocomplex with the gold nanoparticle complex.

The quantum dot and the modified self-illuminative protein may be mixed in a ratio of 1:80 to 1:600.

The crosslinking agent may be 1-ethyl-3-(3-dimethylaminopropyl) carbodiimide (EDC).

The reaction may be performed at room temperature for 60 to 120 minutes.

The self-illuminative nanocomplex and the gold nanoparticle complex may be mixed in a molar ratio of 1:10 to 1:1500.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the present disclosure.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The inventors completed the present disclosure as a result of a study on a self-illuminative nanocomplex exhibiting a high efficiency luminescence activity and a functional cancer medication interacting with the nanocomplex.

Therefore, the present disclosure provides a self-illuminative nanocomplex including a quantum dot and a modified self-illuminative protein consisting of an amino acid sequence of SEQ. ID. NO: 1.

Figure 1:
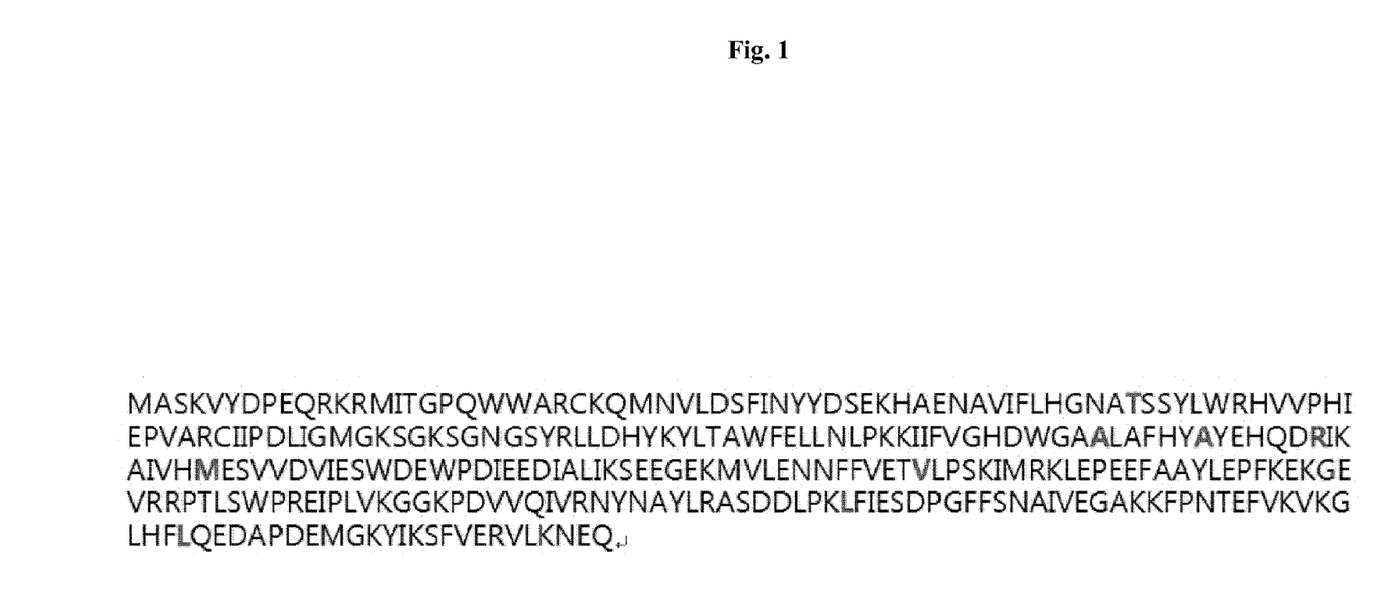
FIG. 1 shows an amino acid sequence (SEQ. ID. NO: 1) of a modified self-illuminative protein (m-Rluc8) prepared by mutation to a wild-type luciferase.

In an embodiment of the present disclosure, to obtain a light source having a high self-illuminate activity, a modified self-illuminative protein (m-Rluc8) consisting of an amino acid sequence of SEQ. ID. NO: 1 and having an excellent luminescence activity, which is approximately 5.6-fold higher than that of the wild type, is produced by performing artificial mutation on a wild-type Renilla luciferase protein at 8 sites, and here, the mutation occurs at position 55, position 124, position 130, position 136, position 143, position 185, position 253 and position 287 in the amino acid sequence (refer to FIG. 1). Therefore, a more stable protein structure is formed by strongly inducing a binding site between a luciferase protein and a substrate (coelenterazine-h) and substituting a thermodynamically unstable hydrophobic site in a protein structure with a hydrophilic amino acid (refer to Example 1). In addition, as a result of an experiment performed with various equivalent ratios of the modified self-illuminative protein (m-Rluc8) and the quantum dot in order to bond the modified self-illuminative protein (m-Rluc8) to the quantum dot and obtain the highest efficiency of a luminescence activity at the quantum dot, it is identified that a nanocomplex prepared by reacting the modified self-illuminative protein (m-Rluc8) with the quantum dot in a ratio of 500:1 emits the strongest light at a wavelength of 800 nm (refer to Example 2).

Here, since the quantum dot and the self-illuminative protein form a chemical bond using a crosslinking agent, a type of the quantum dot is not limited to a specific one. That is, a fluorescence activity of the quantum dot that can be applied to the self-illuminative nanocomplex according to the present disclosure is not limited in a specific wavelength range. Preferably, the quantum dot emitting light at 800 nm in a near-infrared region may be used, and the light in the near-infrared region is advantageous to selective treatment using light due to a small noise in a biological environment.

Therefore, the present disclosure may provide a method of preparing a self-illuminative nanocomplex including a reaction of a quantum dot and a modified self-illuminative protein consisting of an amino acid sequence of SEQ. ID. NO: 1 with a crosslinking agent.

In the present disclosure, the quantum dot and the modified self-illuminative protein may be mixed in a ratio of 1:80 to 1:600, but the present disclosure is not limited thereto.

The crosslinking agent may be 1-ethyl-3-(3-dimethylaminopropyl) carbodiimide (EDC), but may be any one of materials serving to crosslinking a chemical bond between the quantum dot and the self-illuminative protein without limitation.

The self-illuminative nanocomplex may be prepared by reacting the quantum dot, the self-illuminative protein and the crosslinking agent at room temperature for 60 to 120 minutes, and preferably, 90 minutes as described In an exemplary embodiment of the present disclosure, but the present disclosure is not limited thereto. The reaction time may be suitably adjusted by those of ordinary skill in the art according to a condition such as a type of the quantum dot or the crosslinking agent.

In addition, In an exemplary embodiment of the present disclosure, to avoid non-specific reactivity of the self-illuminative nanocomplex in which the quantum dot is bound to the m-Rluc8 protein, a peptide bond (—CONH—) is formed by reacting polyethyleneglycol (PEG) having an —NHS functional group at the end as a hydrophilic polymer with a primary amine group (—NH2) on a surface of the m-Rluc8. In addition, to provide surface specificity of the self-illuminative nanocomplex, a maleimide functional group existing at the other end of the polyethyleneglycol reacts with a thiol group (—SH) existing at 5' end of a targeted cancer-specific molecule, which is a nucleic acid aptamer, thereby chemically bonding the nucleic acid aptamer to the nanocomplex (refer to Example 3).

Accordingly, the present disclosure may provide a target-specific self-illuminative nanocomplex including the self-illuminative nanocomplex, a targeted cancer-specific molecule and a hydrophilic polymer, and a method of treating cancer including treating the target-specific self-illuminative nanocomplex.

Here, since the bond between the targeted cancer-specific molecule and the hydrophilic polymer is a chemical bond and not related to a type of the targeted cancer-specific molecule, there is no limit to a type of the molecule having cancer cell target specificity, which can be used herein. However, a molecule specifically binding to a specific antigen is preferably used, and most preferably a targeted cancer-specific nucleic acid aptamer, an antibody, an enzyme, a PNA, a ligand or a compound is used. In an exemplary embodiment of the present disclosure, as an example of the nucleic acid aptamer molecule, an A10 nucleic acid aptamer is used and known to specifically bind to a cell overexpressing a prostate-specific membrane antigen (PSMA) among prostate cancer cells, and it is identified that an A10 aptamer-binding self-illuminative nanocomplex can specifically enter into prostate cancer (refer to Example 3).

In addition, since there is no limit to a type of the targeted cancer-specific molecule, there is no limit to a type of cancer which can be treated using the self-illuminative nanocomplex of the present disclosure, and preferably, solid cancer overexpressing a cancer-specific antigen such as prostatic cancer, lung cancer, breast cancer, gastric cancer, liver cancer, rectal cancer, cystic duct carcinoma, colon cancer, pancreatic cancer, ovarian cancer, bronchial cancer or bladder cancer is treated.

Here, as the hydrophilic polymer, any one which can inhibit a non-specific interaction between the nanocomplex and the cell through a screening effect may be used without limitation, and preferably, a material such as polyethyleneglycol (PEG), polyvinyl alcohol (PVA) or polyvinylacetate (PVAc), and most preferably, polyethyleneglycol (PEG) is used according to an exemplary embodiment of the present disclosure.

Therefore, to develop a functional cancer medication interacting with the self-illuminative nanocomplex, the inventors prepared a functional cancer medication by physically capturing an anticancer drug in a linear nucleic acid having a thiol group (—SH) at 5' end, and chemically binding gold nanoparticles. That is, in an exemplary embodiment of the present disclosure, a linear nucleic acid complex containing an anticancer drug was prepared by binding linear nucleic acids consisting of base sequences of SEQ. ID. NOs: 2 and 3 and an anticancer drug, for example, doxorubicin (refer to Example 4-1).

Here, an aromatic ring of the anticancer drug is inserted into the sequence of the linear nucleic acid, and particularly, prefers a specific sequence (5'-CG-3' or 5'-GC-3') of the linear nucleic acid. Accordingly, as an anticancer drug capable of binding to the linear nucleic acid of the present disclosure, an anticancer drug having an aromatic ring, for example, an anticancer drug having an aromatic ring to be physically contained in a nucleic acid and break a cell metabolic pathway may be used without limitation, and an anticancer drug such as doxorubicin, daunorubicin, mitoxantrone or epirubicin is preferably bound.

In addition, since a thiol group (—SH) is linked to 5' end of the linear nucleic acid containing the anticancer drug, the linear nucleic acid easily binds to gold nanoparticles by a covalent bond. Therefore, in an exemplary embodiment of the present disclosure, a functional cancer medication was prepared by binding the gold nanoparticles to the linear nucleic acid containing the anticancer drug (refer to Example 4-2). When the gold nanoparticles are irradiated with near-infrared rays, a surface temperature of the gold nanoparticles increases, and thus the release of the anticancer drug binding to the linear nucleic acid may be stimulated.

As described above, since the self-illuminative nanocomplex of the present disclosure emits light at 800 nm and the functional cancer medication exhibits an anticancer effect in response to specific light at 800 nm, it is possible to release the anticancer drug by the interaction between two types of nanoparticle structures without an external laser light source.

Figure 9:
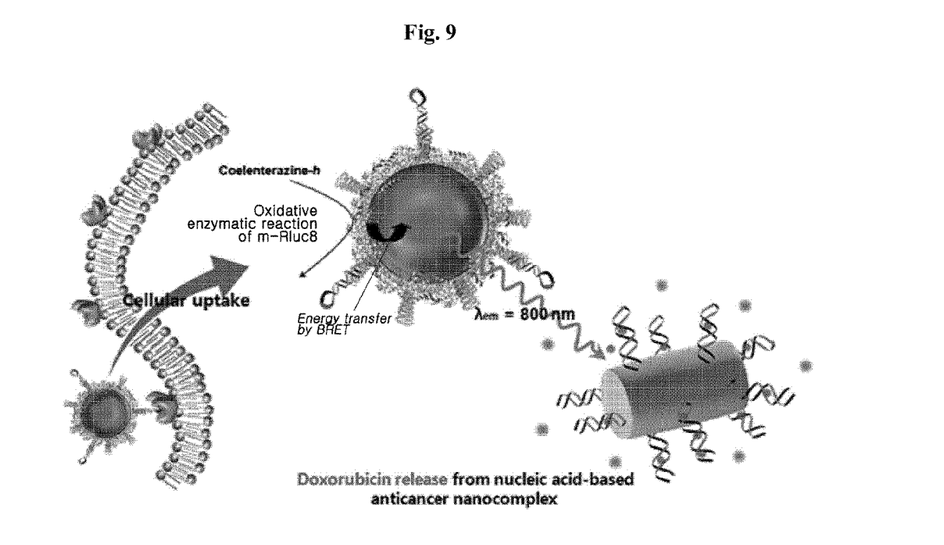
FIG. 9 shows a schematic diagram simply illustrating an action pathway of the self-illuminative nanocomplex and the new functional drug interacting with the nanocomplex.

In this context, In an exemplary embodiment of the present disclosure, it was identified that a release amount of an anticancer drug, doxorubicin, is increased by the interaction between the self-illuminative nanocomplex and the functional cancer medication (refer to Example 5), and it was identified that the self-illuminative nanocomplex binds to a nucleic acid aptamer specifically binding to a cell overexpressing a prostate-specific membrane antigen to have specificity to targeted cancer, i.e., prostate cancer (refer to Example 3). That is, since the self-illuminative nanocomplex according to the present disclosure has target specificity, all mechanisms for treating cancer are specific to target cells, and a schematic diagram illustrating a mechanism of the self-illuminative nanocomplex and the functional cancer medication is shown in FIG. 9.

Accordingly, the present disclosure may provide a method of treating cancer which includes treating a composition including a functional cancer medication including gold nanoparticles binding to a linear nucleic acid complex containing an anticancer drug and the self-illuminative nanocomplex.

The linear nucleic acid may have a thiol group (—SH) binding to 5' end. The linear nucleic acid is preferably a linear nucleic acid having a specific base sequence (5'-CG-3' or 5'-GC-3') at 5' end, and most preferably, a linear nucleic acid consisting of a base sequence of SEQ. ID. NO: 3, but the present disclosure is not limited thereto.

In addition, the gold nanoparticles may be prepared by removing and washing a surfactant, cetyltrimethylammonium bromide (CTAB), from a gold nanoparticle solution before reacting with the linear nucleic acid complex containing an anticancer drug, but pure gold nanoparticles may be used without limitation.

As a result, since the self-illuminative nanocomplex of the present disclosure has target specificity and enables to dramatically improve difficulties in conventional optical treatment, the self-illuminative nanocomplex is expected to provide a new standard for nanoptic therapeutics.

Hereinafter, to help in understanding the present disclosure, exemplary embodiments are provided. However, the following embodiments are only provided to more easily understand the present disclosure, not to limit the present disclosure.

Example 1

Expression of Modified Self-Illuminative Protein (m-Rluc8)

To obtain a high efficiency self-luminescent light source, a modified self-illuminative protein (m-Rluc8) in which artificial mutation occurred on an amino acid sequence of a wild-type luciferase was expressed in *E. coli* and purified. That is, an expression vector (m-Rluc8_pPAL7) into which the modified self-illuminative protein (m-Rluc8) consisting of an amino acid sequence (SEQ. ID. NO: 1) shown in FIG. 1 was inserted was manufactured, transformed into and expressed in *E. coli* BL21 strain cells and then purified, thereby obtaining a high purity modified self-illuminative protein (m-Rluc8).

Figure 2:
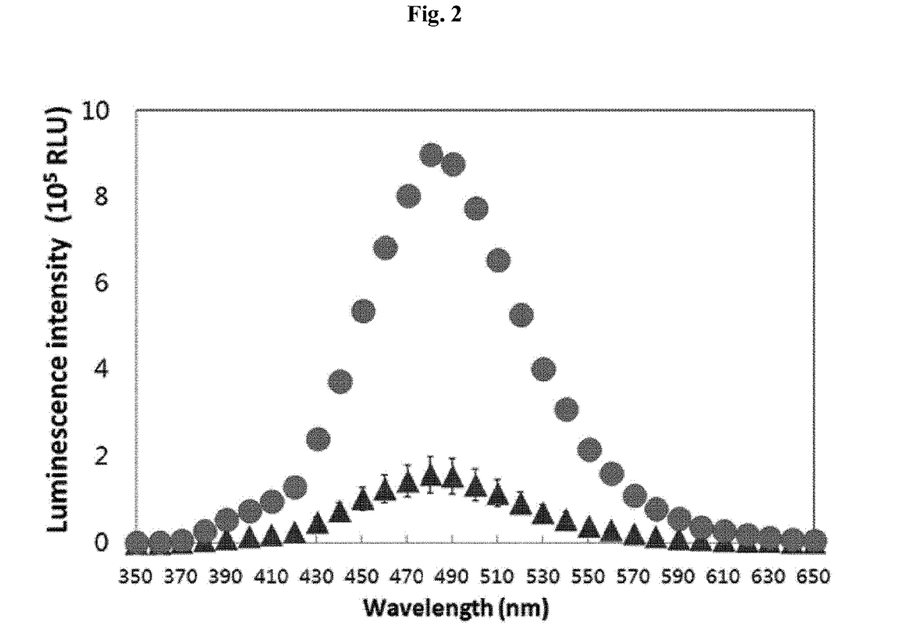
FIG. 2 shows a graph showing that the modified self-illuminative protein (m-Rluc8) has a 5.65-fold higher luminescence activity than a wild-type luciferase, in which a red circle denotes the modified self-illuminative protein, and a blue circle denotes the wild-type luciferase protein.

As a result of the comparison in luminescence activity with the wild-type luciferase purified by the above-described method, as shown in FIG. 2, it was identified that the self-illuminative protein exhibited more than 5.65-fold higher luminescence efficiency.

Example 2

Preparation of Self-Illuminative Nanocomplex

Through the bond between the modified self-illuminative protein (m-Rluc8) and a quantum dot, a nanocomplex having a self-illuminate activity in an 800 nm region was prepared. The self-illuminative nanocomplex was self-luminous due to a bioluminescence resonance energy transfer (BRET) phenomenon between the modified self-illuminative protein (m-Rluc8) and the quantum dot.

To prepare the nanocomplex showing the highest luminescence activity at 800 nm in a near-infrared region, the inventors prepared nanocomplexes with various equivalence ratios of the quantum dot and the modified self-illuminative protein (m-Rluc8). Specifically, the ratio of the self-illuminative protein per 20 pmole of the quantum dot varied in a range of 80, 120, 160, 200, 240, 280, 320, 400, 500 and 600 folds, and these two components reacted with 2 mM of 1-ethyl-3-(3-dimethylaminopropyl)carbodiimide crosslinking agent at room temperature for 90 minutes. The crosslinking agent was used to chemically bind a carboxyl group (—COOH) to a primary amine group (—NH2) on a surface of the modified self-illuminative protein, thereby forming a peptide bond (—CONH—), and thus the modified self-illuminative protein (m-Rluc8) around the quantum dot had a multilayer structure. Therefore, when the self-illuminative protein emitted light, light with a wavelength of 800 nm was also emitted through a BRET phenomenon at the quantum dot. Here, when an outermost protein was gradually spaced apart from the quantum dot due to the expansion of the multilayer structure of the modified protein (m-Rluc8) around the quantum dot, even if more modified proteins (m-Rluc8) were bound, a critical point which did not affect luminescence efficiency of the quantum dot was made. That is, even if more proteins were bound, after the critical point, the luminescence efficiency at the wavelength of 800 nm was not increased, but the amount of light at a wavelength of 487 nm in a light emitting region of the modified self-illuminative protein (m-Rluc8) was continuously increased.

Figure 3:
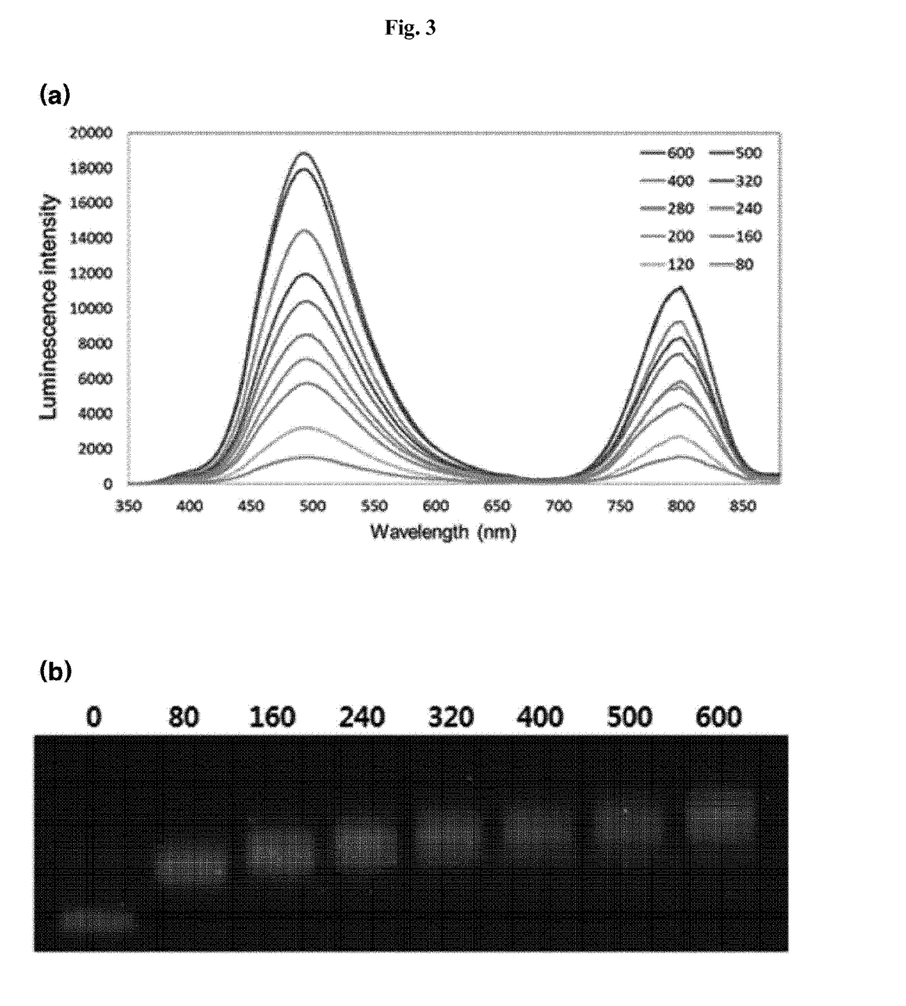
FIG. 3 shows (a) a graph showing a luminescence activity and (b) images obtained by agarose gel electrophoresis according to a change in molecular weight, when the modified self-illuminative protein (m-Rluc8) reacts with a quantum dot in various equivalence ratios.

As a result of detecting the critical point according to a ratio of the modified self-illuminative protein (m-Rluc8), as shown in FIG. 3A, it was determined that, even if a 500-fold or higher equivalence ratio of the modified self-illuminative protein (m-Rluc8) than that of the quantum dot was added for reaction, the luminescence activity at 800 nm was not increased any more.

In addition, as a result of electrophoresis conducted under conditions including a 0.5% agarose gel, 0.5×TAE running buffer and 100 V, as shown in FIG. 3B, it was seen that the modified self-illuminative protein (m-Rluc8) had differences in degree of electrophoretic mobility according to a degree of binding to the quantum dot.

Example 3

Identification of Target Specificity of Self-Illuminative Nanocomplex

To prevent random endocytosis of the self-illuminative nanocomplex and enhance target specificity, polyethyleneglycol and an A10 nucleic acid aptamer chemically bound to a surface of the self-illuminative nanocomplex. Since a highly hydrophilic material, polyethyleneglycol, can inhibit a non-specific interaction between the nanocomplex and a cell through a screening effect, polyethyleneglycol consisting of 24 oxyethylene monomers and having all of an —NHS functional group and a maleimide functional group at both ends was used. The functional groups reacted with a primary amine (—NH?) and a carboxyl group (—COOH) at room temperature to rapidly form a chemical bond. Therefore, the self-illuminative nanocomplex, the polyethyleneglycol and the A10 nucleic acid aptamer were mixed in a ratio of 1:100:100, and reacted at 25° C. for 90 minutes, thereby forming an self-illuminative nanocomplex having target specificity. To examine whether the self-illuminative nanocomplex was specifically transferred into cells, prostate cancer cells (LNCaP cell line) and prostate cancer cells (PC3 cell line) as a control were seeded in a 24-well plate to have a cell count of $1 \times 10^5$ cells, and cultured under condition of 37° C. and 5% $CO_2$ for 24 hours. In addition, after 10 nM of an A10 and polyethyleneglycol-binding self-illuminative nanocomplex or an only polyethyleneglycol-binding self-illuminative nanocomplex per cell line was reacted for 2 hours, self-illuminative nanocomplexes remaining outside the cells were removed by changing the medium with fresh RPMI 1640 medium, and a fluorescence intensity of the self-illuminative nanocomplex entering into the cells was detected using flow cytometry.

Figure 4:
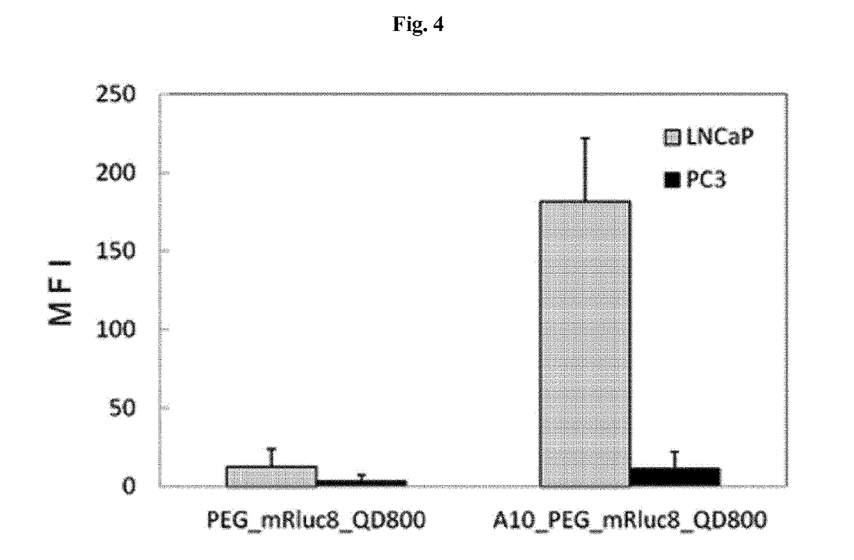
FIG. 4 shows a graph showing a result for target-specific endocytosis of an self-illuminative nanocomplex.

As a result, as shown in FIG. 4, it was determined that the self-illuminative nanocomplex having an A10 nucleic acid aptamer showed a considerably higher targeted cell specificity than the self-illuminative nanocomplex not having an A10 nucleic acid aptamer.

The above result means that the A10 aptamer of the self-illuminative nanocomplex bound to a prostate-specific membrane antigen (PSMA) to transfer the self-illuminative nanocomplex into the cells, and therefore, the self-illuminative nanocomplex can be effectively transferred into desired cancer cells.

Example 4

Preparation of Functional Cancer Medication

<4-1> Preparation of Linear Nucleic Acid Containing Doxorubicin Anticancer Drug

To contain doxorubicin in a new nucleic acid-based functional anticancer drug, linear nucleic acids represented by SEQ. ID. NO: 2 (5'-CGAGTAGGTACGGATCTGGCT-GTACTGATGTGCCTGCGAC-3') and SEQ. ID. NO: 3 (5'-/thiol/GTCGCAGGCACATCAGTACAGCCAGATC-CGTACCTACTCG-3') were used. To prepare a doxorubicin-binding linear nucleic acid, the linear nucleic acid and doxorubicin were mixed with various concentrations (linear nucleic acid:doxorubicin=1:1 to 1:20) and reacted at room temperature for 24 hours, and autofluorescence of the doxorubicin was detected. When doxorubicin was captured in the linear nucleic acid, the concentration of doxorubicin remaining in the solution was decreased, and the autofluorescence caused by doxorubicin was also decreased.

Figure 5:
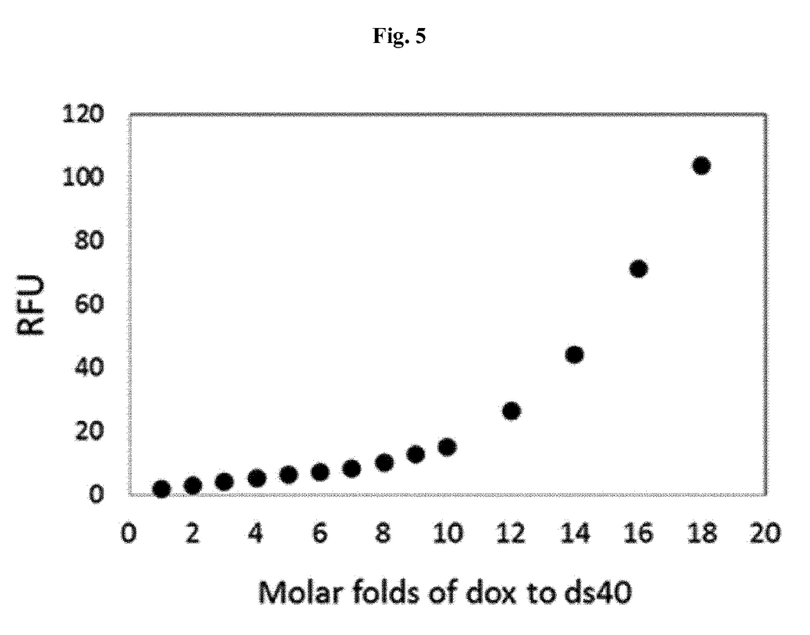
FIG. 5 shows a result obtained by measuring an intensity of autofluorescence changed according to a degree to which doxorubicin is contained in a linear nucleic acid.

As a result, as shown in FIG. 5, it was shown that fluorescence intensity was decreased by decreasing the concentration of doxorubicin remaining in the solution, and almost the same fluorescence intensities were exhibited in concentration ratios of 1:10 or less.

It means that the maximum 10 μM doxorubicin may bind to 1 μM linear nucleic acid, and an optimal mixing ratio to prepare a linear nucleic acid/doxorubicin complex is 1:10.

<4-2> Preparation of Linear Nucleic Acid Containing Doxorubicin Anticancer Drug and Gold Nanoparticle Complex Since the linear nucleic acid of SEQ. ID. NO: 3 has a thiol group (—SH) at 5' end, the linear nucleic acid easily makes a covalent bond with gold nanoparticles. To bind the gold nanoparticles with the anticancer drug-containing nucleic acid structure, the gold nanoparticles were washed once using a centrifugal separator to remove cetyltrimethylammonium bromide (CTAB), the washed gold nanoparticles were mixed and reacted with the anticancer drug-containing nucleic acid structure at room temperature for 16 hours. The prepared multifunctional nucleic acid-based anticancer drug was separated from unbinding anticancer drug-containing nucleic acid structures and gold nanoparticles through centrifugation. To identify the prepared complex of the gold nanoparticles and the anticancer drug-containing linear nucleic acid, a surface potential of a gold nanoparticle structure was detected using an electrophoresis light scattering apparatus. The gold nanoparticles before reacting with the linear nucleic acid structure has a positive surface potential because of a CTAB bilayer, and the linear nucleic acid structure has a strong negative charge.

Figure 6:
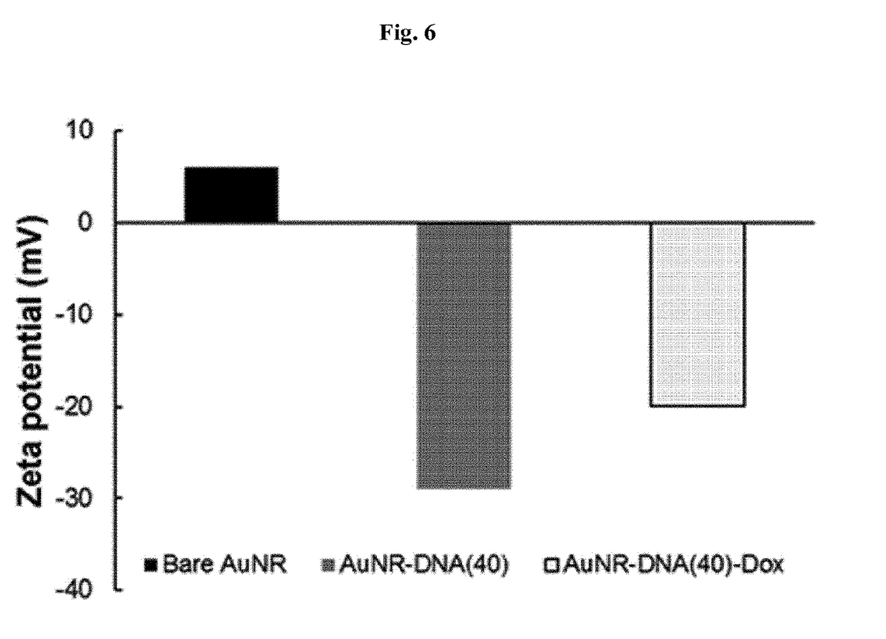
FIG. 6 shows a result obtained by measuring a change in surface characteristic of a gold nanoparticle structure before and after a linear nucleic acid containing doxorubicin binds to a surface of the gold nanoparticle structure.

As a result, as shown in FIG. 6, it was shown that the complex of the gold nanoparticles and the anticancer drug-containing linear nucleic acid had a negative charge.

As described above, as a functional cancer medication, the complex of the gold nanoparticles and the anticancer drug-containing linear nucleic acid was prepared.

Example 5

Identification of Release of Doxorubicin by Self-Illuminative Nanocomplex and Functional Cancer Medication Interacting with the Nanocomplex To identify the release of doxorubicin from a functional cancer medication by interaction with a high efficiency self-illuminative nanocomplex, the release of doxorubicin was identified by measuring fluorescence intensity after reaction of 5 pmole and 10 pmole of an self-illuminative nanocomplex, 7.4 nM of a functional cancer medication, and 5 mg of coelenterazine-h.

Figure 7:
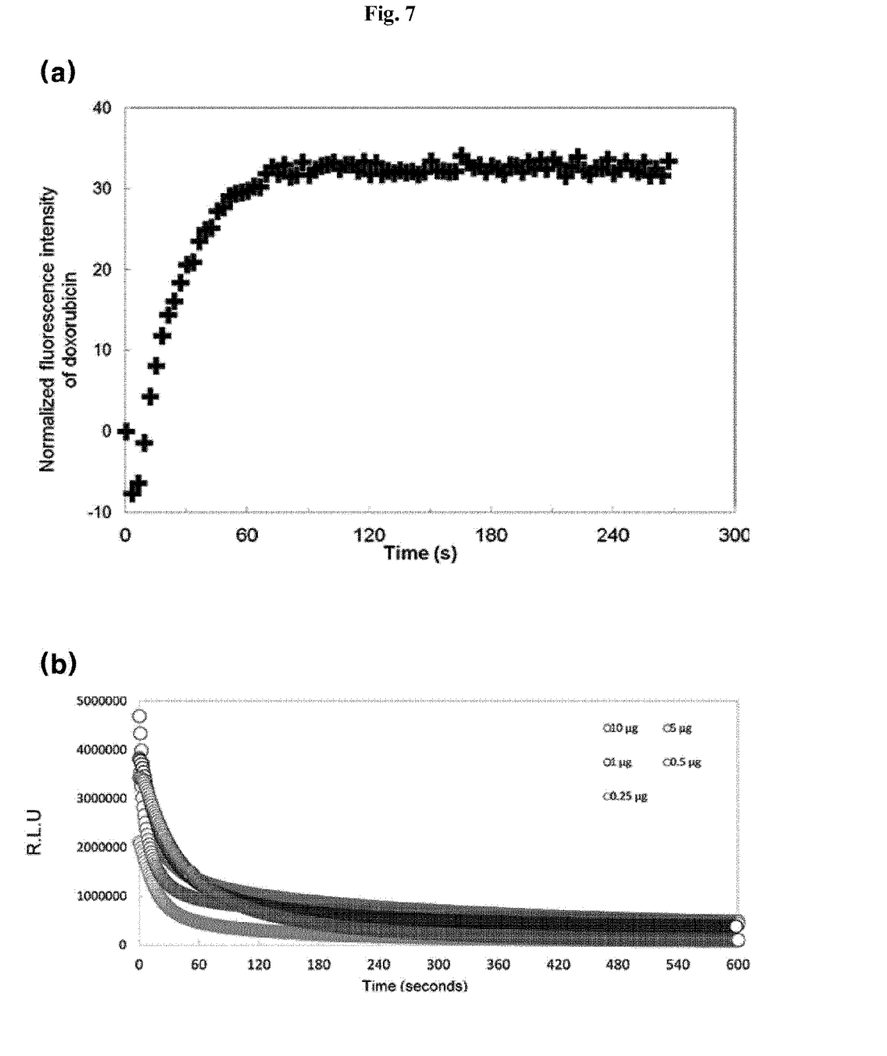
FIG. 7 shows a graph showing a doxorubicin release effect caused by an self-illuminative nanocomplex and a new functional drug interacting with the nanocomplex.

As a result of measuring the fluorescence intensity, as shown in FIG. 7A, it was determined that the fluorescence intensity of doxorubicin was increased for approximately 90 seconds from the time at which light was emitted by the coelenterazine-h. This is the result that the concentration of doxorubicin remaining in the solution was increased by releasing doxorubicin, and the autofluorescence intensity caused by doxorubicin was increased.

The result shows that, when 5 pmole and 10 pmole of the self-illuminative nanocomplex and the coelenterazine-h are reacted, as shown in FIG. 7B, a luminescence amount after approximately 90 seconds has a strong cause-and-effect relationship with an equilibrium state.

That is, the result clearly shows that doxorubicin is effectively released by interaction between the self-illuminative nanocomplex and the functional cancer medication interacting therewith, and it is possible to have active interaction between the nanocomplex and the functional cancer medication.

Example 6

Identification of Cancer Cell Death Effect by Self-Illuminative Nanocomplex and Functional Cancer Medication Interacting with the Nanocomplex To identify an anticancer effect of an self-illuminative nanocomplex and a new functional anticancer agent interacting with the nanocomplex, prostate cancer cells were seeded in an 96-well plate to have a cell count of $1 \times 10^5$ cells, and cultured under conditions of 37° C. and 5% $CO_2$ for 24 hours. In addition, 10 pmole of the self-illuminative nanocomplex and 10 μM (concentration of contained doxorubicin) of a functional anticancer agent interacting with the nanocomplex were added to the cells and reacted for 2 hours, and then 5 mg of coelenterazine-h was also added to the resulting mixture. Afterward, the cells were further cultured for 24 hours, and then the cell death effect was identified using a WST-1 cell viability assay. As a control and comparative groups, 10 μM of doxorubicin, 10 pmole of the self-illuminative nanocomplex (RQ), and 10 μM of the new functional anticancer agent (DDA) were used.

Figure 8:
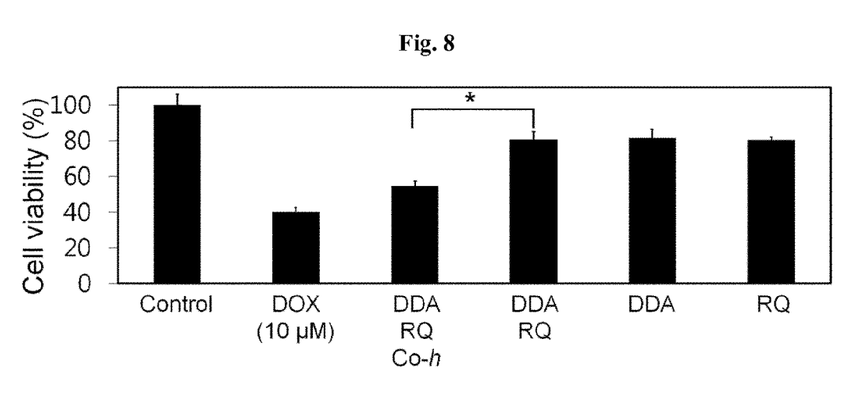
FIG. 8 shows a result for an experiment showing a cancer cell death effect caused by the nanocomplex and the new functional drug interacting with the nanocomplex.

Consequently, as shown in FIG. 8, the self-illuminative nanocomplex and the new functional anticancer agent interacting with the nanocomplex according to the present disclosure did not exhibit an effective cell toxicity in vitro. However, when coelenterazine-h was added, an apparent cancer cell death effect was identified (n=3, *p<0.05).

The above-described result clearly shows that doxorubicin was effectively released by interaction of the self-illuminative nanocomplex and the new functional anticancer agent interacting with the nanocomplex, and therefore a prostate cancer cell death effect was exhibited. In addition, the above-described result shows an ultimate object of the present disclosure in which, according to an active interaction between the self-illuminative nanocomplex and the new functional anticancer agent interacting with the nanocomplex, an active anticancer effect can be obtained without an external laser light source.

In a high efficiency self-illuminative nanocomplex of the present disclosure, a high efficiency modified self-illuminative protein (m-Rluc8) shows a strong luminescence activity at a wavelength band of 487 nm, and strong light is emitted from a quantum dot at 800 nm through BRET with a quantum dot located in a nano-scale short distance. The light is light energy in a near-infrared region frequently used in anticancer treatment using laser, and thus a targeted cancer cell may be treated by interaction with a new anticancer drug specifically responding to 800-nm light like a functional cancer medication. In addition, as polyethyleneglycol and a nucleic acid aptamer having target specificity formed thereon are chemically bound to a surface of the high efficiency self-illuminative nanocomplex of the present disclosure, an effect of a corresponding nanocomplex to a normal cell, which is not a target, can be minimized, and thus the nanocomplex can have high target specificity. Problems of conventional laser treatment are expected to be fundamentally solved by performing a series of laser treatment in a targeted cancer cell by adding a nanometer-sized laser light source and a functional cancer medication interacting therewith to the targeted cancer cell, and therefore it is expected to propose a new paradigm of nanoptic therapeutics.

While the disclosure has been shown and described with reference to certain exemplary embodiments thereof, it will be understood by those skilled in the related art that various changes in form and details may be made therein without departing from the scope of the disclosure as defined by the appended claims.

What is claimed is:

1. A method of preparing a composition for treating cancer, comprising:
   (a) preparing a self-illuminative nanocomplex by mixing a quantum dot, a modified self-illuminative protein consisting of an amino acid sequence of SEQ. ID. NO: 1 and a crosslinking agent;
   (b) preparing a linear nucleic acid containing an anticancer drug by mixing a linear nucleic acid consisting of the sequence of SEQ ID NO: 3 and having a thiol group at 5' end and an anticancer drug in a molar ratio of 1:10 to 1:20; and
   (c) preparing a gold nanoparticle complex by mixing the linear nucleic acid containing the anticancer drug and gold nanoparticles from which cetyltrimethylammonium bromide (CTAB) is removed,
   wherein the self-illuminative nanocomplex and the gold nanoparticle complex are capable of being combined to form a composition for treating cancer.

2. The method according to claim 1, wherein the quantum dot and the modified self-illuminative protein are mixed in a molar ratio of 1:80 to 1:600.

3. The method according to claim 1, wherein the crosslinking agent is 1-ethyl-3-(3-dimethylaminopropyl)carbodiimide (EDC).

4. The method according to claim 1, wherein the mixing of the step (a) is performed at room temperature for 60 to 120 minutes.

5. The method according to claim 1, wherein the self-illuminative nanocomplex and the gold nanoparticle complex are mixed in a molar ratio of 1:10 to 1:1500.

6. The method according to claim 1, further comprising: reacting a hydrophilic polymer with the modified self-illuminative protein.

7. The method according to claim 6, wherein the hydrophilic polymer is selected from the group consisting of polyethyleneglycol (PEG), polyvinyl alcohol (PVA), and polyvinylacetate (PVAc).

8. The method according to claim 1, wherein in step (b) the anticancer drug has an aromatic ring inserted into a sequence of the linear amino acid.

9. The method according to claim 8, wherein the anticancer drug is selected from the group consisting of doxorubicin, daunorubicin, mitoxantrone, and epirubicin.

10. The method according to claim 8, wherein the aromatic ring is inserted into a 5'-CG-3' or a 5'-GC-3' sequence of linear nucleic acid.

11. The method according to claim 1, wherein in step (a) the crosslinking agent forms a peptide bond between the quantum dot and the modified self-illuminative protein.

12. The method according to claim 11, wherein the modified self-illuminative protein is formed into a multi-layer structure around the quantum dot.

13. A method of preparing a composition for cancer treatment, comprising:
   (a) preparing a first component, comprising crosslinking a quantum dot with a modified self-illuminative protein consisting of an amino acid sequence of SEQ ID NO: 1 to thereby form a nanocomplex;
   (b) preparing a second component, comprising (i) mixing a linear nucleic acid consisting of the sequence of SEQ ID NO: 3 with an anticancer drug to thereby form a linear nucleic acid/drug complex, and (ii) mixing the linear nucleic acid/drug complex with gold nanoparticles,
   wherein the first component and the second component are capable of being combined to thereby form a reactive composition for cancer treatment.

14. A method of targeting administration of an anticancer drug, comprising:
   (a) administering to a subject a self-illuminative protein having
      (i) a quantum dot crosslinked to the self-illuminative protein such that illumination of the self-illuminative protein at one wavelength yields emission of light of a different wavelength from the quantum dot by bioluminescence resonance energy transfer (BRET), and (ii) having a target cell-specific moiety attached to the self-illuminative protein to mediate endocytosis by the target cell; and (b) administering to the subject a gold nanoparticle having
(i) a plurality of linear nuclear acids consisting of the sequence of SEQ ID NO: 3 covalently bound to a surface of the gold nanoparticle, and
(ii) an anti-cancer drug physically captured in the plurality of linear nucleic acids;

wherein the self-illuminative protein and the gold nanoparticle are each administered to the subject in an amount effective to release a therapeutic amount of the anticancer drug through heating the surface of the gold nanoparticle by emission of light of the different wavelength from the quantum dot.

* * * * *

SEQUENCE LISTING

```
<160> NUMBER OF SEQ ID NOS: 3

<210> SEQ ID NO 1
<211> LENGTH: 311
<212> TYPE: PRT
<213> ORGANISM: Renilla luciferase

<400> SEQUENCE: 1

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270
```

```
Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 2
<211> LENGTH: 40
<212> TYPE: DNA
<213> ORGANISM: Artificial Sequence
<220> FEATURE:
<223> OTHER INFORMATION: single strand linear DNA

<400> SEQUENCE: 2
cgagtaggta cggatctggc tgtactgatg tgcctgcgac                          40

<210> SEQ ID NO 3
<211> LENGTH: 40
<212> TYPE: DNA
<213> ORGANISM: Artificial Sequence
<220> FEATURE:
<223> OTHER INFORMATION: single strand linear DNA

<400> SEQUENCE: 3
gtcgcaggca catcagtaca gccagatccg tacctactcg                          40
```